United States Patent [19]

Martin et al.

[11] Patent Number: 5,008,285

[45] Date of Patent: Apr. 16, 1991

[54] (6,11-DIHYDRO-11-OXODIBENZ[b,e]OXE-PIN-YL)PENTANOIC ACIDS AND DERIVATIVES THEREOF

[75] Inventors: Lawrence L. Martin, Lebanon; Linda L. Setescak, Somerville, both of N.J.

[73] Assignee: Hoechst-Roussel Pharmaceuticals, Inc., Somerville, N.J.

[21] Appl. No.: 430,045

[22] Filed: Nov. 1, 1989

Related U.S. Application Data

[63] Continuation-in-part of Ser. No. 252,328, Oct. 3, 1988, abandoned, which is a continuation of Ser. No. 945,626, Dec. 23, 1986, abandoned, which is a continuation of Ser. No. 604,672, Apr. 27, 1984, abandoned.

[51] Int. Cl.$^5$ .................. A61K 31/335; C07D 313/12
[52] U.S. Cl. .................................... 514/450; 549/354
[58] Field of Search .................. 549/354; 514/450

[56] References Cited

U.S. PATENT DOCUMENTS 4,238,620  12/1980  Uno et al. ............................ 549/354

FOREIGN PATENT DOCUMENTS 2435613  7/1979  Fed. Rep. of Germany ...... 549/354
2319339  6/1976  France ................................ 549/354

*Primary Examiner*—Frederick E. Waddell
*Assistant Examiner*—Ba K. Trinh
*Attorney, Agent, or Firm*—Elliott Korsen

[57] ABSTRACT

Novel (6,11-dihydro-11-oxodibenz[b,e]oxepinyl)pentanoic acids and derivatives thereof, intermediates and processes for the preparation thereof, and methods for suppressing arthritis-like inflammation utilizing compounds or compositions thereof are disclosed.

2 Claims, No Drawings

(6,11-DIHYDRO-11-OXODIBENZ[b,e]OXEPIN-YL)PENTANOIC ACIDS AND DERIVATIVES THEREOF

This is a continuation-in-part of co-pending application Ser. No. 252,328 filed Oct. 3, 1988 now abandoned, which is a continuation of application Ser. No. 945,626 filed Dec. 23, 1986, now abandoned, which is a continuation of application Ser. No. 604,672 filed Apr. 27, 1984, now abandoned.

The present invention relates to (6,11-dihydro-11-oxodibenz[b,e]oxepinyl)pentanoic acids and derivatives thereof. More particularly, the present invention relates to (6,11-dihydro-11-oxodibenz[b,e]oxepinyl)pentanoic acids of acids of formula 1

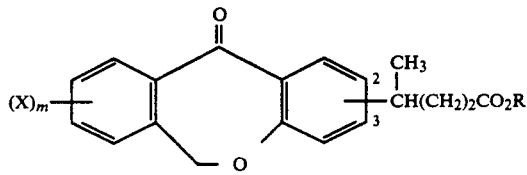

wherein R is hydrogen or loweralkyl of 1 to 5 carbon atoms; x is hydrogen, loweralkyl of 1 to 5 carbon atoms, loweralkoxy of 1 to 5 carbon atoms, halogen or trifluoromethyl; and m is 1 or 2, the optical antipode thereof or a pharmaceutically acceptable salt thereof, which are useful as antiarthritic agents, alone or in combination with inert pharmaceutical carriers.

Prefered compounds of the present invention are those wherein R and X are hydrogen and the group

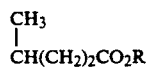

is bound to either the 2- or 3-position of the dibenz[b,e]oxepin ring.

The present invention also relates to alkyl [(2-carboalkoxybenzyloxy)phenyl]pentanoates of formula 2

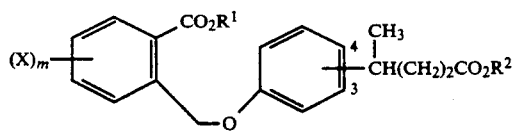

wherein $R^1$ is hydrogen or loweralkyl of 1 to 5 carbon atoms; $R^2$ is hydrogen or loweralkyl of 1 to 5 carbon atoms with the proviso that $R^1$ and $R^2$ are simultaneously hydrogen or loweralkyl of 1 to 5 carbon atoms; X is hydrogen, loweralkyl of 1 to 5 carbon atoms; loweralkoxy of 1 to 5 carbon atoms, halogen or trifluoromethyl; and m is 1 or 2, or the optical antipode thereof, and alkyl (hydroxyphenyl)pentanoates of formula 3

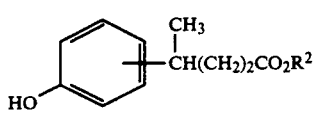

wherein and $R^2$ is loweralkyl of 1 to 5 carbon atoms, or an optical antipode thereof, useful as intermediates for the preparation of the hereinbeforementioned (6,11-dihydro-11-oxodibenz[b,e]oxepin)pentanoic acids and derivatives thereof.

Prefered alkyl [(2-carboalkoxybenzyloxy)phenyl]-pentanoates are those wherein $R^2$ is loweralkyl of 1 to 5 carbon atoms, X is hydrogen and the group

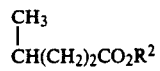

is bound to either the 3- or 4-position of the benzyloxyphenyl ring.

Prefered alkyl (hydroxyphenyl)pentanoates are those wherein the group

is bound to either 3- or 4-position of the phenolic ring.

As used through the specification and appended claims, the term "alkyl" refers to a straight or branched chain hydrocarbon radical containing no unsaturation and having 1 to 5 carbon atoms such as methyl, ethyl, 1-propyl, 2-propyl, 1-butyl, 1-pentyl, 2-pentyl, and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, pentanoic acid and the like; the term "halogen" refers to a member of the family fluorine, chlorine, bromine or iodine. The term "lower" as applied to any of the aforementioned groups refers to a group having a carbon skeleton containing up to and including 5 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diasteromeric salts of those instant compounds characterized by the presence of an acidic carboxylic acid group and an optically active base, or by the synthesis from optically active precursors.

The present invention comprehends all optical isomers and racemic forms thereof of the compounds disclosed and claimed herein. The formulas of the compounds shown herein are intended to encompass all possible optical isomers of the compounds so depicted.

The novel (6,11-dihydro-11-oxodibenz[b,e]oxepinyl)-pentanoic acids 1 of the present invention are synthesized by the processes illustrated in Reaction Scheme A.

Condensation of a benzylhaloester 4 with a phenolic ester 3 provides a benzyloxyester 2 which is hydrolyzed to a benzyloxyacid 5 and, in turn, cyclized to a (6,11-dihydro-11-oxodibenz[b,e]oxepinyl)pentanoic acid 6. The pentanoic acid 6 may be esterified to the ester 8.

The condensation is accomplished by contacting a benzylhalo ester 4 with a phenolic ester 3 in an alkanone in the presence of an alkali metal carbonate. Among alkanones there may be mentioned 2-propanone, 2-butanone, 3-pentanone, and the like. Among alkali metal carbonates there may be mentioned lithium, sodium and potassium carbonate and the like. 2-Butanone and potassium carbonate and the prefered alkanone and alkali metal carbonate, respectively. The temperature at which the condensation is conducted is not critical. However, to assure a reasonable rate of reaction, the condensation is preferably performed at the reflux temperature of reaction medium.

A condensation promotor such as an alkali metal halide, for example, lithium, sodium or potassium bromide, or lithium, sodium or potassium iodide, may be employed. Potassium iodide is the prefered promotor.

The hydrolysis is affected by treating a diester 2 with an alkali metal hydroxide such as lithium hydroxide, sodium hydroxide, potassium hydroxide and the like in an aqueous alkanol such as methanol, ethanol, 1- and 2-propanol, 2,2-dimethylethanol, pentanol, and the like. Potassium hydroxide and aqueous ethanol is the prefered reaction medium. The hydrolysis may be accomplished at ordinary temperatures. To facilitate the reaction, however, elevated temperatures falling within the range of ambient temperature to the reflux temperature of the reaction medium may be employed. The reflux temperature of the reaction medium is prefered.

The cyclization is preferably conducted by contacting a diacid 5 with trifluoroacetic anhydride in a halocarbon solvent, such as dichloromethane, trichloromethane, tetrachloromethane, 1,1-dichloroethane, 1,2-dichloroethane, and the like. The cyclization temperature is not narrowly critical. The reaction is accomplished at ambient temperature (25° C.) to the reflux temperature of the reaction medium. The reflux temperature of the reaction medium is prefered.

The cyclization proceeds efficiently when two or more molar-equivalents of trifluoroacetic anhydride (relative to diacid 5) are employed. It is preferable to conduct the cyclization employing about two to about six molar-equivalents of trifluroacetic anhydride, and most preferable to employ about three molar equivalents of the cyclizing agent.

The cyclization of a diacid 5 to an oxepinonepentanoic acid 6 may be affected by means of phosphorous-containing agents such as phosphorous pentoxide, phosphorous pentoxide-alkanol, polyphosphoric acid-alkanoic acid and the like. For example, treatment of a diacid 5 with phosphorous pentoxide or phosphorous pentoxide-ethanol in the presence or absence of a solvent, such as sulfolane, at ambient to moderate temperatures within the range of about 25° to 120° C., (a cyclization temperature of about 90° C. being prefered), and treatment of diacid 5 with polyphosphoric acid or polyphosphoric acid-acetic acid at ambient to moderate temperatures within the range of about 25° to 100° C., (a reaction temperature of about 80° C. being prefered), affords oxepinone 6.

The cyclization of diacid 5 to oxepinonepentanoic acid 6 via diacid halide 7 may also be achieved by means of Friedel-Crafts reagents. For example, treatment of diacid chloride 7, which may be prepared from diacid 5 by contacting it with a halogenating agent such as phosphorous trichloride or thionyl chloride, with catalytic or excess amounts (e.g., about 0.001 to about 10 molar-equivalents of Friedel-Crafts reagent to diacid chloride 7) of aluminium chloride, stannic chloride, ferric chloride, and the like in a halocarbon solvent (e.g., dichloromethane, 1,2-dichloromethane, 1,1,2,-trichloroethylene, and the like) at reduced to moderate temperatures (e.g., about 0° to about 120° C.) yields oxepinonepentanoic acid 6, after hydrolysis.

A (6,11-dihydro-11-oxodibenz[b,e]oxepinyl)pentanoic acid 6 may be transformed to the corresponding ester 8, i.e., an alkyl (6,11-dihydro-11-oxodibenz[b,e]oxepinyl)pentanoate of formula 8, by esterification procedures. For example, a pentanoic acid 6 may be treated with an alkanol in the presence of a mineral acid such as sulfuric acid, hydrochloric acid, hydrobromic acid, and the like, or a strong organic acid such as methanesulfonic acid, 4-methylphenylsulfonic acid, and the like to afford ester 8.

Benzylhaloester 4 is prepared by procedures described and referenced in D. E. Aultz, et al., J. Med. Chem., 20, 66 (1977).

Phenolic ester 3 is prepared by the sequence depicted in Scheme B, involving esterification of nitrophenylpentanoic acid 9 to alkyl nitrophenylpentanoate 10, followed by reduction of alkyl nitrophenylpentanoate 10 to alkyl aminophenylpentanoate 11 and conversion of alkyl aminophenyl pentanoate 11 to alkyl hydroxyphenylpentanoate 3. Thus, treatment of acid 9 with an alkanol, e.g., ethanol, in the presence of a mineral acid, e.g., sulfuric acid, provides ester 10, which is reduced to aniline 11 with hydrogen in the presence of a hydrogenation catalyst, e.g., palladium-on-carbon, and, in turn, diazotized with nitrous acid, generated in situ from an alkali metal nitrite, e.g., sodium nitrite, and a mineral acid, e.g., sulfuric acid, to a diazonium salt and, without isolation, hydrolyzed to the phenol 3 by means of aqueous copper sulfate solution.

The (6,11-dihydro-11-oxodibenz[b,e]oxepinyl)pentanoic acids and derivatives thereof of the present invention are useful as antiarthritic agents due to their ability to suppress arthritis-type inflammation in mammals. The antiarthritic utility is demonstrated in the adjuvant-induced polyarthritis syndrome in rats, by a procedure similar to that described by C. M. Perron and F. D. Wood, Arthritis and Rheumatism, 2, 440 (1959).

Groups of 10 male Charles River-Wistar Lewis rats weighing 150 to 175 g were individually housed and maintained on a regular rat chow diet. Water was given ad libitrim. The adjuvant was prepared by suspending 75 mg of *Mycobacterium butyricum* (Defco Laboratories, Detroit, Mich.) in 10 ml of white paraffin oil with continuous stirring for 2 hrs at room temperature prior to administration. Test compounds are prepared by suspending the drug in water, adding one drop of Tween 80 per 10 ml of suspension, and homogenizing. The adjuvant suspension (0.1 ml) was injected into the footpad of the left hind paw of the rat. Test compound suspensions were administered orally (10 ml/kg) the day before adjuvant suspension injection and the administration was continued for 21 days. One group of ten rats was used for the test drug, standard, adjuvant-injected control and non-injected control. Control animals received vehicle (10 ml/kg). Three doses of test drug and one dose of standard preparation were used. Injected and non-injected paw volumes were determined on the day the adjuvant suspension was given, and on subsequent days thereafter (usually days 5, 10, 18, and " the method of C. A. Winter, et al., Proc. Soc. Exp. Biol. Med., 111, 544 (1962).

The percent inhibition of paw volume (injected and non-injected hind paw) was calculated by the following formula:

$$\% \text{ Inhibition} = \frac{\substack{\text{Mean Paw Volume} \\ \text{Change of Injected} \\ \text{(or Non-injected) Control}} - \substack{\text{Mean Paw Volume} \\ \text{Change of Drug} \\ \text{Treated}}}{\substack{\text{Mean Paw Volume Change of} \\ \text{Injected (or Non-Injected) Control}}} \times 100$$

$ED_{50}$-values, i.e., the dose at which the drug affects a 50% inhibition of paw volume, were estimated by the method of J. T. Litchfield and F. Wilcoxon, J. Pharm. Exp. Ther., 96, 99 (1948) and statistically evaluated by means of the student "t" test. $ED_{50}$-values of a compound of the present invention and a standard are presented below:

| Compound | $ED_{50}$ (mg/kg/day) |
|---|---|
| 4-(6,11-dihydro-11-oxodibenz[b,e]oxepin-2-yl)pentanoic acid | 6.4 (injected) 3.4 (non-injected) |
| Phenylbutazone | 12 (injected) 6.8 (non-injected) |

Arthritic-like inflammation suppression is achieved when the present (6,11-dihydro-11-oxodibenz[b,e]oxepinyl)pentanoic acids are administered to a subject requiring such treatment as an effective oral, parenteral or intraveous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judment of the person administering or supervising the administration of the aforesaid compound. It is to be further understood that the dosages set forth herein are exemplary only and that they do not, to any extent, limit the scope or practice of the invention.

The compounds of the present invention also exhibit surprisingly low ulcerogenic activity. (The ulcerogenic activity test is hereafter referred to as GI). The GI test method is reported at J. Med. Chem., 20, 66,69 (1977). The ulcerogenic activity of a compound of this invention compared with the propionic acid homolog is presented below:

| Compound | GI $ID_{50}$(mg/kg p.o.) |
|---|---|
| 2-(6,11-Dihydro-11-oxodibenz[b,e]-oxepin-2-yl)propionic acid | 5.5 |
| 4-(6-11-Dihydro-11-oxodibenz-[b,e]-oxepin-2-yl)pentanoic acid | >100.0 |

Effective amounts of a compound of the present invention may be administered to a subject by any one of various methods, for example, orally as in capsules or tablets, parenterally in the form of sterile solutions or suspensions, and in some cases intravenously in the form of sterile solutions. The (6,11-dihydro-11-oxodibenz[b,e]oxepinyl)pentanoic acids of the present invention, while effective themselves, may be formulated and administered in the form of their pharmaceutically acceptable addition salts for purposes of stability, convenience of crystallization, increased solubility and the like.

The (6,11-dihydro-11-oxodibenz[b,e]oxepinyl)pentanoic acids of the present invention form addition salts with pharmaceutically acceptable non-toxic bases. Preferred bases include inorganic bases such as ammonia, alkali metal hydroxides, for example, lithium, sodium and potassium hydroxides, and alkaline earth hydroxides, for example, calcium and magnesium hydroxides, and organic bases such as mono-, di- or trialkyamines, for example, ethyl, diethyl and triethylamine, and mono-, di- and trihydroxyalkyl amines such as, for example, 2-hydroxyethylamine, di-2-hydroxyethylamine, and tri-2-hydroxyethylamine.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose; a disintegrating agent such as alginic acid, Primogel ®, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

While the (6,11-dihydro-11-oxodibenz[b,e]oxepinyl)-pentanoic acids of the present invention exhibit antiarthritic activity in the adjuvant-induced polyarthritis syndrome assay as hereinbefore discussed, the present compounds are essentially inactive antiinflammatories in an art-recognized assay for antiinflammatory activity, the carrageenen paw assay (D. E. Aultz, et al., J. Med. Chem., 20, 66 (1977)).

The (6,11-dihydro-11-oxodibenz[b,e]oxepinyl)pentanoic acids of the present invention are also essentially inactive analgetics in an art-recobnized assay for analgesia, the phenyl-para-benzoquinone assay for analgetic activity (E. Siegmund, et al., proc. Soc. Exptl. Biol. Med., 95, 729 (1957)).

The following examples are for illustration purposes only and are not to be construed as limiting the invention. All temperatures are given in degrees centigrade (°C.).

EXAMPLE 1

Ethyl 4-(4-nitrophenyl)pentanoate

A mixture of 110 g of 4-(4-nitrophenyl)valeric acid, 600 ml of absolute ethanol and 10 ml of concentrated sulfuric was heated under reflux overnight. The ethanol was evaporated in vacuo and the residue was partitioned between ether and water. The ether extract was washed with 5% of sodium bicarbonate solution and water, dried over anhydrous sodium sulfate, filtered and evaporated to give 119 g (97%) of product, bp 127°-128° (1.5 mm).

REACTION SCHEME A

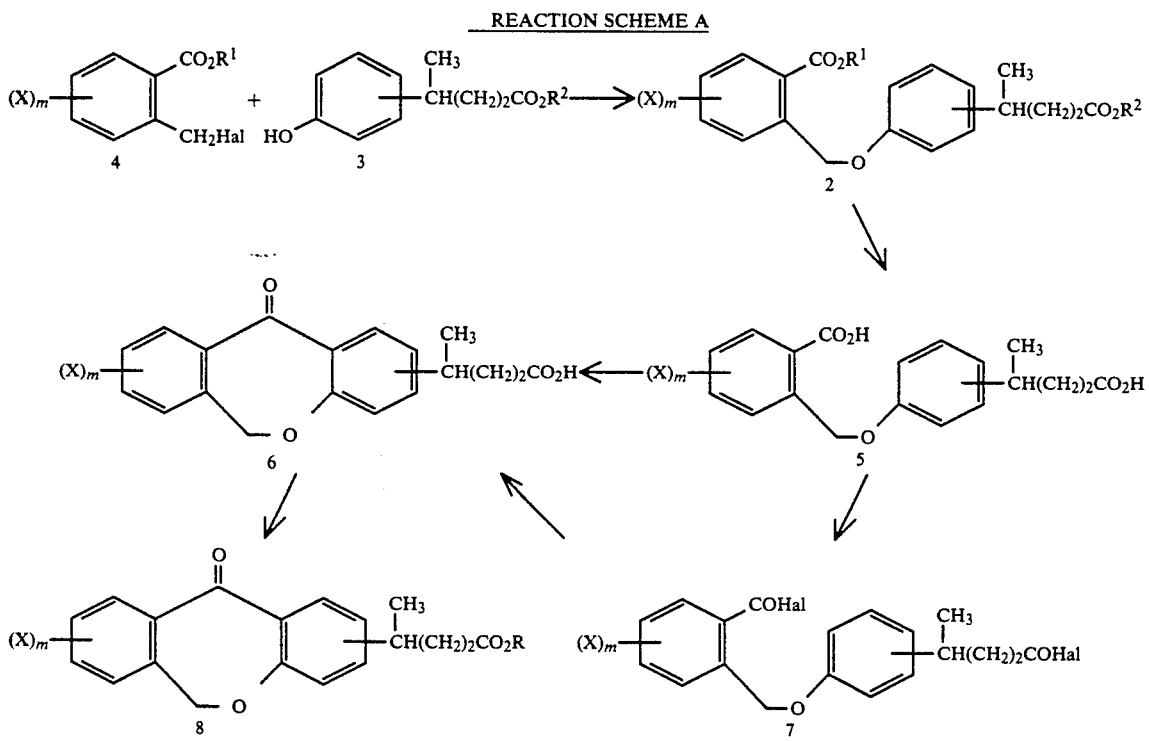

wherein R, $R^1$, $R^2$, X, Hal and m are as hereinbeforedescribed.

REACTION SCHEME B

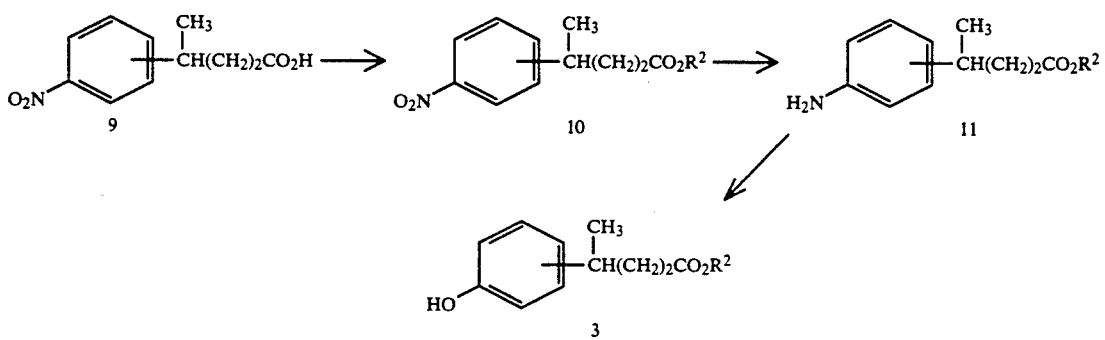

wherein $R^2$ is as hereinbeforedescribed.

| ANALYSIS | | | |
|---|---|---|---|
| Calculated for $C_{13}H_{17}NO_4$ | 62.14% C | 6.82% H | 5.58% N |
| Found | 62.28% C | 6.92% H | 5.45% N |

EXAMPLE 2

Ethyl 4-(4-aminophenyl)pentanoate

A mixture of 114 g of ethyl 4-(4-nitrophenyl)pentanoate, 170 ml of absolute ethanol and 2 g of 10% of palladium-on-charcoal was hydrogenated on a Paar shaker until consumption of hydrogen ceased. The catalyst was collected and the ethanol evaporated. The residue was partitioned between water and ether. The ether extract was washed with 5% of sodium bicarbonate solution and water, dried over anhydrous sodium sulfate, filtered and evaporated to give 85 g (86%) of product, bp 118°–122° C. (0.55–0.60 mm).

| ANALYSIS | | | |
|---|---|---|---|
| Calculated for $C_{13}H_{19}NO_2$ | 70.56% C | 8.65% H | 6.33% N |
| Found | 70.69% C | 8.64% H | 6.18% N |

EXAMPLE 3

Ethyl 4-(4-hydroxyphenyl)pentanoate

To a solution of 350 g concentrated sulfuric acid and 350 ml of water, cooled to 0°, 40 g of ethyl 4-(4-aminophenyl)pentanoate was added dropwise, maintaining the temperature at 0°–2°. The mixture was treated dropwise with a solution of 13.66 g of sodium nitrite in 25 ml of water at a rate such that the temperature did not exceed 2°. The solution was added dropwise to a refluxing solution of 387 g of copper sulfate in 600 ml of water over a period of about 30 min and the resultant mixture was heated under reflux for an additional 10 min. The mixture was cooled to room temperature, 800 ml of water was added, and extracted thrice with dichloromethane (additional water was needed to dissolve the salts). The organic phase was washed with water, dried over anhydrous sodium sulfate, filtered and evaporated. The residue was distilled at 129° (0.6 mm) to give 21.05 g (53%) of product, mp 32°–34°.

| ANALYSIS | | |
|---|---|---|
| Calculated for $C_{13}H_{18}O_3$ | 70.25% C | 8.16% H |
| Found | 69.98% C | 8.19% H |

EXAMPLE 4

Ethyl 4-[4-(2-ethoxycarbonylbenzyloxy)phenyl]pentanoate

A mixture of 12 g of ethyl 4-(4-hydroxyphenyl)pentanoate, 16.05 g of ethyl -bromo-o-toluate, 0.5 g of pulverized potassium iodide and 36.49 g of potassium carbonate in 300 ml of 2-butanone was heated under reflux overnight. The salts were collected and washed with ether. The filtrate was evaporated and the residue was partitioned between water and ether. The organic layer was separated, washed with 10% sodium hydroxide solution and water, dried over anhydrous sodium sulfate, filtered and evaporated. Chromatography on a Waters Associates Prep LC-System 500 (two silica gel columns; elution with dichloromethane) gave 12.15 g (59%) of product, as an oil.

| ANALYSIS | | |
|---|---|---|
| Calculated for $C_{23}H_{28}O_5$ | 71.85% C | 7.34% H |
| Found | 71.68% C | 7.16% H |

EXAMPLE 5

4-[4-(2-carboxybenzyloxy)phenyl]pentanoic acid

A mixture of 14 g of ethyl 4-[4-(2-ethoxycarbonylbenzyloxy)-phenyl]pentanoate, 31 g of potassium hydroxide in 40 ml of water and 250 ml of 95% of ethanol was heated under reflux overnight. The solution was concentrated and the residue was dissolved in water, cooled and acidified with cold conc hydrochloric acid. The mixture was extracted with ether, and the extract was dried over anhydrous sodium sulfate, filtered and evaporated. Trituration with hexane afforded 8.9 g (72%) of product, mp 104°–106°. Recrystallization from acetonitrile gave an analytical sample, mp 115°–117.5°.

| ANALYSIS | | |
|---|---|---|
| Calculated for $C_{19}H_{20}O_5$ | 69.50% C | 6.14% H |
| Found | 69.48% C | 6.17% H |

EXAMPLE 6

4-(6,11-Dihydro-11-oxodibenz[b,e]oxepin-2-yl)pentanoic acid

To a solution of 6.91 g of 4-[4-(2-carboxybenzyloxy)phenyl]pentanoic acid in 70 ml of dichloromethane, 13.26 g of trifluoracetic anhydride was added dropwise. The mixture was heated under reflux for five hrs. The mixture was cooled, water was added dropwise, and the resultant mixture was stirred 0.5 hrs. The organic layer was separated, washed with water, dried over anhydrous sodium sulfate, filtered and evaporated. Trituration with hexane followed by recrystallization from acetonitrile gave 3.75 g (58%) of product, mp 120°–124° C.

| ANALYSIS | | |
|---|---|---|
| Calculated for $C_{19}H_{18}O_4$ | 73.53% C | 5.85% H |
| Found | 73.69% C | 5.92% H |

We claim:

1. A method of suppressing arthritic inflammation with low gastric irritability in mammals which comprises orally administering to a mammal in need of arthritic type inflammation suppression with low gastric irritability an effective amount of a compound of the formula

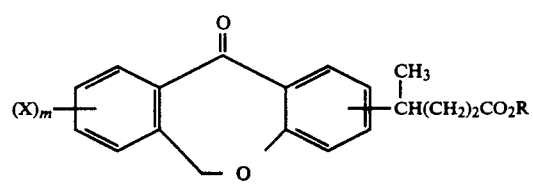

wherein R is hydrogen or loweralkyl of 1 to 5 carbon atoms; X is hydrogen, loweralkyl of 1 to 5 carbon atoms, loweralkoxy of 1 to 5 carbon atoms, halogen or trifluoromethyl, and m is 1 or 2, the optical antipode thereof; or a pharmaceutically acceptable salt thereof.

2. The method according to claim 1 wherein the compound is 4-(6,11-dihydro-11-oxodibenz[b,e]oxepin-2-yl)pentanoic acid.

* * * * *